(12) United States Patent
Sun et al.

(10) Patent No.: US 11,786,522 B2
(45) Date of Patent: Oct. 17, 2023

(54) ARIPIPRAZOLE INJECTABLE SUSPENSION FORMULATION HAVING PROLONGED SHELF LIFE

(71) Applicant: Nanjing Noratech Pharmaceuticals Co., Ltd, Nanjing (CN)

(72) Inventors: Yunzhe Sun, Nanjing (CN); Qi Peng, Nanjing (CN); Cheng-Gang Lin, Nanjing (CN); Li Gui, Nanjing (CN); Zhihui Liu, Nanjing (CN); Fei Liu, Nanjing (CN)

(73) Assignee: Nanjing Noratech Pharmaceuticals Co., LTD, Nanjing (CN)

( * ) Notice: Subject to any disclaimer, the term of this patent is extended or adjusted under 35 U.S.C. 154(b) by 191 days.

(21) Appl. No.: 15/755,801

(22) PCT Filed: Mar. 16, 2016

(86) PCT No.: PCT/CN2016/076454
§ 371 (c)(1),
(2) Date: Feb. 27, 2018

(87) PCT Pub. No.: WO2017/036118
PCT Pub. Date: Mar. 9, 2017

(65) Prior Publication Data
US 2019/0070171 A1     Mar. 7, 2019

(30) Foreign Application Priority Data

Aug. 31, 2015  (CN) .......................... 201510546844.0

(51) Int. Cl.
| | | |
|---|---|---|
| A61K 31/496 | (2006.01) | |
| A61K 9/10 | (2006.01) | |
| A61K 47/38 | (2006.01) | |
| A61P 25/18 | (2006.01) | |
| A61K 9/00 | (2006.01) | |
| A61K 47/26 | (2006.01) | |

(52) U.S. Cl.
CPC .......... *A61K 31/496* (2013.01); *A61K 9/0019* (2013.01); *A61K 9/10* (2013.01); *A61K 47/26* (2013.01); *A61K 47/38* (2013.01); *A61P 25/18* (2018.01)

(58) Field of Classification Search
CPC ........ A61K 31/496; A61K 47/26; A61K 9/10; A61K 9/0019; A61K 47/38; A61P 25/18
See application file for complete search history.

(56) References Cited

U.S. PATENT DOCUMENTS

| | | | |
|---|---|---|---|
| 7,456,181 B2 | 11/2008 | Parthasaradhi et al. | |
| 7,491,726 B2 | 2/2009 | Parthasaradhi et al. | |
| 7,504,504 B2 | 3/2009 | Aronhime et al. | |
| 7,642,353 B2 | 1/2010 | Ettema et al. | |
| 7,655,798 B2 | 2/2010 | Ettema et al. | |
| 7,807,680 B2 | 10/2010 | Kostanski et al. | |
| 7,902,198 B2 | 3/2011 | Ettema et al. | |
| 7,910,589 B2 | 3/2011 | Bando et al. | |
| 8,008,490 B2 | 8/2011 | Wieser et al. | |
| 8,030,313 B2 | 10/2011 | Kostanski et al. | |
| 8,338,427 B2 | 12/2012 | Brown | |
| 8,338,428 B2 * | 12/2012 | Brown ................. | A61K 31/496 514/327 |
| 8,399,469 B2 | 3/2013 | Bando et al. | |
| 8,722,679 B2 | 5/2014 | Kostanski et al. | |
| 8,759,351 B2 | 6/2014 | Brown | |
| 8,993,761 B2 | 3/2015 | Bando et al. | |
| 9,089,567 B2 | 7/2015 | Jordan et al. | |
| 10,080,746 B2 | 9/2018 | Liu et al. | |
| 10,525,057 B2 | 1/2020 | Raoufinia | |
| 10,913,721 B2 | 2/2021 | Sun et al. | |
| 10,980,803 B2 | 4/2021 | Raoufinia | |
| 11,154,553 B1 | 10/2021 | Raoufinia | |
| 2008/0107745 A1 * | 5/2008 | Kostanski ............ | A61K 9/0019 424/489 |

FOREIGN PATENT DOCUMENTS

| | | | |
|---|---|---|---|
| CN | 101801342 A | | 8/2010 |
| CN | 102846543 | * | 1/2013 |
| CN | 102846543 A | | 1/2013 |
| JP | 2014-129343 A | | 7/2014 |

OTHER PUBLICATIONS

Translation CN 102846543 (Year: 2013).*
PubChem CID443314 [online] Polysorbate 20; created on Jun. 24, 2005, pp. 1-37, [Retrieved on Apr. 2, 2019], <url: https://pubchem.ncbi.nlm.nih.gov/compound/443314> (Year: 2005).*
PubChem CID23672064 [online] (Monosodium phosphate;created on Feb. 5, 2008, pp. 1-91 Retrieved on: Apr. 2, 2019 <url: https://pubchem.ncbi.nlm.nih.gov/compound/23672064#section=Top> (Year: 2008).*
PubChem CID 5281955 [online] Retrieved on Jan. 6, 2020, Retrieved from the internet <url: https://pubchem.ncbi.nlm.nih.gov/compound/Polyoxyethylene-sorbitan-monooleate> (Year: 2006).*
International Search Report for PCT/CN2016/076454 dated Jun. 20, 2016.
Brittain, Harry G. Aripiprazole: Polymorphs and Solvatomorphs. Profiles of Drug Substances, Excipients, and Related Methodolgy, vol. 37. ISSN: 1871-5125, DOI: 10.1016/B978-0-12-3977220-0.00001-5. (2012).
Aoki, Satoshi, et al. Study of Crystal Transformation of Aripiprazol. Otsuka Pharmaceutical Co., Ltd. CR119. Japan. Translation. Oct. 6, 1996.
Abilify Highlights of Prescribing Information. Dec. 2014.

* cited by examiner

*Primary Examiner* — Shobha Kantamneni
(74) *Attorney, Agent, or Firm* — Sorell, Lenna & Schmidt, LLP

(57) ABSTRACT

The present invention belongs to the field of pharmaceutical formulation, and particularly relates to an aripiprazole injectable suspension formulation having prolonged shelf life, and methods of using the formulation in treating schizophrenia and related diseases. In another aspect, the present invention also relates to a method of prolonging shelf life of an aripiprazole injectable suspension formulation.

4 Claims, 1 Drawing Sheet

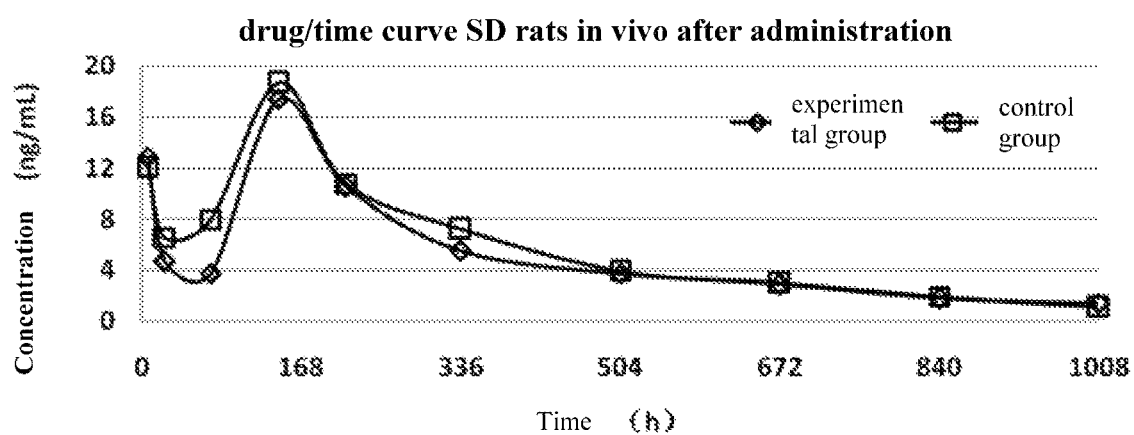

ARIPIPRAZOLE INJECTABLE SUSPENSION FORMULATION HAVING PROLONGED SHELF LIFE

FIELD OF THE INVENTION

The present invention belongs to the field of pharmaceutical formulation, and particularly relates to an aripiprazole injectable suspension formulation having prolonged shelf life, and methods of using the formulation in treating schizophrenia and related diseases. In another aspect, the present invention also relates to a method of prolonging shelf life of an aripiprazole injectable suspension formulation.

BACKGROUND OF THE INVENTION

Aripiprazole, as an antagonist of dopamine neurotransmitter, was used in treating schizophrenia, other mental disorders and central nervous system disorders. In the treatment of schizophrenia, long-acting aripiprazole injectable formulation can increase patient's compliance to reduce the recurrence rate, and effectively improve patient's social interaction ability and quality of life.

Abilify Maintena has been approved by the FDA as a long-acting injectable formulation. However, the original research company pointed out that after long-term storage, particles would aggregate and settle from the aripiprazole suspension, and hard to be redispersed. Therefore, Abilify Maintena was prepared as lyophilized powder using freeze-dried technology (see CN 101801342 B), and redispersed by injectable water upon use. In addition, although CN 102133171 A also disclosed a long-acting injectable formulation of aripiprazole, it does not mention the problem that particles would aggregate and settle from the aripiprazole suspension after long-term storage and hard to be redispersed.

In order to reduce the production costs, simplify the production process and be convenient for patients to use, the present invention overcomes the drawback that "particles would aggregate and settle from the aripiprazole suspension after long-term storage and hard to be redispersed," and provides a method of prolonging shelf life of an aripiprazole injectable suspension formulation, as well as a stable injectable suspension formulation of aripiprazole having prolonged shelf life.

BRIEF SUMMARY OF THE INVENTION

An objective of the present invention is to provide a stable injectable suspension formulation of aripiprazole having prolonged shelf life, while maintaining the long-acting and sustained-release properties similar to known formulations.

The objectives of the present invention are achieved by the following technical solutions.

The present invention provides an aripiprazole injectable suspension formulation having prolonged shelf life, characterized in that, it comprises a cellulose-based suspending agent and polyoxyethylene (20) sorbitan monooleate.

According to the invention, the combination of cellulose-based suspending agent and polyoxyethylene (20) sorbitan monooleate is especially suitable for preparing aripiprazole suspension injectable formulation, so as to overcome the drawback that particles would aggregate and settle from the aripiprazole suspension after long-term storage and hard to be redispersed. The cellulose-based suspending agent used in the present invention includes but is not limited to a methyl cellulose, a carboxymethyl cellulose, a hydroxyl propylmethyl cellulose, or a hydroxypropyl cellulose.

In one embodiment, the ratio (by weight) of the cellulose-based suspending agent to the polyoxyethylene (20) sorbitan monooleate in the aripiprazole injectable suspension formulation of the invention is 1:0.5 to 1:6, preferably 1:0.5 to 1:3, and more preferably 1:0.5, 1:1, 1:2 or 1:3.

In one embodiment, the aripiprazole injectable suspension formulation of the invention further comprises mannitol.

In one embodiment, the aripiprazole injectable suspension formulation of the invention is a sustained release sterile injectable preparation in the form of an aqueous suspension. After injection, the injectable formulation sustainedly releases a therapeutic effective amount of aripiprazole during a period of at least 1 week, preferably 2 weeks, 3 weeks or 4 weeks, and up to 6 weeks or longer. Said injection includes intramuscular injection or subcutaneous injection.

In one embodiment, the aripiprazole injectable suspension formulation of the invention further comprises a buffer salt, wherein the buffer salt is a phosphate, preferably a disodium hydrogen phosphate, a sodium dihydrogen phosphate, and more preferably a sodium dihydrogen phosphate.

In one embodiment, the aripiprazole injectable suspension formulation of the invention may comprise aripiprazole, a cellulose-based suspending agent, polyoxyethylene (20) sorbitan monooleate and injectable water, and be adjusted to appropriate pH value; a buffer salt may be further included.

In one embodiment, the aripiprazole injectable suspension formulation of the invention comprises: 50-300 mg/mL of aripiprazole, 2-10 mg/mL of a cellulose-based suspending agent, and 4-48 mg/mL of polyoxyethylene (20) sorbitan monooleate, wherein the ratio (by weight) of the cellulose-based suspending agent to the polyoxyethylene (20) sorbitan monooleate is 1:0.5 to 1:6.

In another embodiment, the amount of aripiprazole is in the range of 50-200 mg/mL, the amount of the cellulose-based suspending agent is in the range of 4-8 mg/mL, the amount of polyoxyethylene (20) sorbitan monooleate is in the range of 4-24 mg/mL, the amount of sodium dihydrogen phosphate is in the range of 0.4-4 mg/mL, and the ratio (by weight) of the cellulose-based suspending agent to the polyoxyethylene (20) sorbitan monooleate is: 1:0.5 to 1:3.

In one embodiment, the amount of aripiprazole is 200 mg per 1 mL of the injectable suspension formulation, the amount of the cellulose-based suspending agent is selected from 4 mg or 8 mg, the amount of mannitol is 40 mg, the amount of polyoxyethylene (20) sorbitan monooleate is selected from 4 mg, 8 mg or 24 mg, the amount of sodium dihydrogen phosphate is 0.6 mg, and the ratio (by weight) of the cellulose-based suspending agent to the polyoxyethylene (20) sorbitan monooleate is: 1:0.5 to 1:3, preferably from 1:0.5, 1:1, 1:2, 1:3, 1:6.

As used herein, the term "therapeutically effective amount" refers to an amount that results in improvement/amelioration of any parameters or clinical symptoms. The actual dose may vary from patient to patient, and does not necessarily refer to the total amount eliminates all disease symptoms.

The aripiprazole pharmaceutical composition of the present invention may comprise aripiprazole in crystalline form (forms B, C, D, E, F, G, etc.) or in amorphous form, salts of aripiprazole, aripiprazole dehydrate or hydrate, especially a hydrate, including conventional hydrate, or hydrate A, solvates (e.g., ethanolate) of aripiprazole, or prodrugs of aripiprazole, or aripiprazole metabolites, all of which can be used in the formulation of the present invention.

Salts of aripiprazole in the present invention refer to those salts that retain the biological effectiveness and properties of the parent compound. Among them, salts formed by acids refer to those obtained by reacting of the free base of the parent compound with an inorganic acid or organic acid. Inorganic acids include but are not limited to hydrochloric acid, hydrobromic acid, nitric acid, phosphoric acid, metaphosphoric acid, sulfuric acid, sulfurous acid and perchloric acid. Organic acids include but are not limited to formic acid, acetic acid, propionic acid, acrylic acid, oxalic acid, (D) or (L) malic acid, fumaric acid, maleic acid, hydroxybenzoic acid, gamma-hydroxybutyric acid, methoxybenzoic acid, phthalic acid, benzoic acid, picolinic acid, methanesulfonic acid, ethanesulfonic acid, naphthalene-1-sulfonic acid, naphthalene-2-sulfonic acid, p-toluenesulfonic acid, trifluoromethanesulfonic acid, tetrafluoroboric acid, fluorophosphoric acid, salicylic acid, tartaric acid, citric acid, lactic acid, mandelic acid, succinic acid or malonic acid, etc.

Prodrugs of aripiprazole in the present invention are inactive derivatives of aripiprazole which would be easily converted to the desired compound in vivo.

Sodium dihydrogenphosphate in the present invention includes anhydrous sodium dihydrogenphosphate, sodium dihydrogenphosphate monohydrate, and sodium dihydrogenphosphate dihydrate, all of which may be used in the formulation of the present invention.

The present invention also provides a method for treating schizophrenia and related diseases, such as bipolar disorder and dementia, comprising the step of administering a therapeutically effective amount of the above-mentioned aripiprazole injectable formulation to a patient in need thereof (may be administered intramuscularly or subcutaneously).

In another aspect, the present invention provides a method for prolonging the shelf life of an aripiprazole injectable suspension formulation, characterized in preparing a vehicle for injection using a cellulose-based suspending agent and polysorbate 80.

In general, methods for preparing an aripiprazole injectable suspension formulation include the step of dispersing aripiprazole in a vehicle for injection. The vehicle for injection may contain suspending agents, buffer salts, etc.

The method of the present invention is characterized in that a vehicle for injection is formulated using a cellulose-based suspending agent and polysorbate 80. The cellulosic-based suspending agent described herein includes but is not limited to methyl cellulose, carboxymethyl cellulose, hydroxypropylmethyl cellulose, and hydroxypropyl cellulose.

In one embodiment, the ratio (by weight) of the cellulose-based suspending agent to the polyoxyethylene (20) sorbitan monooleate is 1:0.5 to 1:6, preferably 1:0.5 to 1:3, and more preferably 1:0.5, 1:1, 1:2 or 1:3.

The term "prolonged shelf life" as used herein refers to the period in which particles would not aggregate and settle from the aripiprazole suspension after storage at ambient temperature (e.g., 25° C.) or at elevated temperature (e.g., 40° C. or above). The prolonged shelf life is at least 1 month, preferably at least 2-4 months, more preferably at least 5-6 months and even more preferably at least 6 months.

BRIEF DESCRIPTION OF THE SEVERAL VIEWS OF THE DRAWINGS

FIG. 1 shows the drug-time curve in experimental group and control group SD rats within 1008 h after administration of drug.

DETAILED DESCRIPTION OF THE INVENTION

The present invention is further illustrated in detail in conjunction with the embodiments as follows. However, the scope of the present invention is not limited thereto.

Example 1: Preparation of Aripiprazole Suspension

Formula

TABLE 1

| | Formula 1 | Formula 2 | Formula 3 | Formula 4 | Formula 5 | Comparison example 1 | Comparison example 2 |
|---|---|---|---|---|---|---|---|
| aripiprazole | 400 mg | 400 mg | 400 mg | 400 mg | 400 mg | 400 mg | 400 mg |
| Sodium carboxymethyl cellulose | 16 mg | 8 mg | 8 mg | 16 mg | 16 mg | / | 16 mg |
| Mannitol | 80 mg | 80 mg | 80 mg | 80 mg | 80 mg | 80 mg | 80 mg |
| polyoxyethylene (20)sorbitan monooleate | 8 mg | 8 mg | 16 mg | 48 mg | 96 mg | 16 mg | / |
| Polyoxyethylene (20)sorbitan monolaurate | / | / | / | / | / | / | 16 mg |
| Sodium dihydrogen phosphate monohydrate | 1.38 mg | 1.38 mg | 1.38 mg | 1.38 mg | 1.38 mg | 1.38 mg | 1.38 mg |
| Injectable water | Appropriate amount, adjust to 2 mL | Appropriate amount, adjust to 2 mL | Appropriate amount, adjust to 2 mL | Appropriate amount, adjust to 2 mL | Appropriate amount, adjust to 2 mL | Appropriate amount, adjust to 2 mL | Appropriate amount, adjust to 2 mL |

Preparation Methods

Formulae 1-5:

Method 1:

(1) sodium carboxymethyl cellulose, mannitol, polyoxyethylene (20) sorbitan monooleate, buffer salt was dissolved in an appropriate amount of water for injection, and filtered through 0.22 μm membrane for sterilization;

(2) add sterilized aripiprazole to the material obtained in step 1 and disperse evenly;

(3) process the material obtained in step 2 to appropriate particle size, add water for injection to adjust to target concentration, and aliquot.

Method 2:

(1) process sterilized aripiprazole to appropriate particle size;

(2) prepare an aqueous solution containing sodium carboxymethyl cellulose, mannitol, sorbitan monooleate and buffer salts of polyoxyethylene (20), and filter it through 0.22 μm membrane for sterilization;

(3) mix materials obtained in steps 1 and 2, add water for injection to adjust to target concentration, and aliquot.

Comparison Example 1

(1) mannitol, polyoxyethylene (20)sorbitan monolaurate, buffer salt was dissolved in an appropriate amount of water for injection, and filtered through 0.22 μm membrane for sterilization;

(2) add sterilized aripiprazole to the material obtained in step 1 and disperse evenly;

(3) process the material obtained in step 2 to appropriate particle size, add water for injection to adjust to target concentration, and aliquot.

Comparison Example 2

(1) sodium carboxymethyl cellulose, mannitol, polyoxyethylene (20) sorbitan monooleate, buffer salt was dissolved in an appropriate amount of water for injection, and filtered through 0.22 μm membrane for sterilization;

(2) add sterilized aripiprazole to the material obtained in step 1 and disperse evenly;

(3) process the material obtained in step 2 to appropriate particle size, add water for injection to adjust to the target concentration, and aliquot.

Example 2: Stability of Aripiprazole Particle Size in Suspension

Particle size in samples was measured using Malvern 3000 laser particle size analyzer. D10 is the particle size (in micrometers) corresponding to the cumulative particle size distribution percentage of the sample reaching 10%. It is similar for D50, D90. Before measurement, the sample was shaken for 30 seconds, so as to evenly disperse the particles in the suspension. The sample was added to the sample tank (the dispersion medium was purified water), and the data (D10/D50/D90) were read after the absorption was stable. If the sample cannot be shaken to completely dispersed, it is marked as "aggregate."

TABLE 2

Aripiprazole particle size in suspensions under 25° C. measured 0, 1, 2, 3, 4, 5, and 6 months

|  | 25° C., 0 h | 25° C., 1 month | 25° C., 2 months | 25° C., 3 months |
| --- | --- | --- | --- | --- |
| Formula 1 | 0.606/1.93/7.16 | 0.630/2.01/6.79 | 0.628/1.96/6.86 | 0.649/1.94/6.98 |
| Formula 2 | 0.624/1.84/5.00 | 0.638/1.86/5.15 | 0.650/1.92/5.77 | 0.652/1.93/5.80 |
| Formula 3 | 0.461/1.27/4.11 | 0.447/1.20/3.93 | 0.455/1.22/4.01 | 0.455/1.23/4.05 |
| Formula 4 | 0.604/1.92/6.99 | 0.629/1.96/7.01 | 0.636/2.00/7.02 | 0.642/2.04/6.92 |
| Formula 5 | 0.603/1.90/6.85 | 0.634/1.99/6.81 | 0.641/2.01/7.10 | 0.649/1.99/7.12 |
| Comparison example 1 | 0.527/1.43/4.04 | aggregate | aggregate | aggregate |
| Comparison example 2 | 0.588/1.77/5.98 | 0.609/1.82/6.16 | aggregate | aggregate |

|  | 25° C., 4 months | 25° C., 5 months | 25° C., 6 months |
| --- | --- | --- | --- |
| Formula 1 | 0.640/1.98/6.94 | 0.639/2.00/6.80 | 0.633/2.00/6.70 |
| Formula 2 | 0.661/1.86/5.24 | 0.642/1.86/5.24 | 0.665/1.88/5.23 |
| Formula 3 | 0.462/1.23/3.95 | 0.455/1.21/3.97 | 0.460/1.24/4.06 |
| Formula 4 | 0.641/1.99/7.05 | 0.650/2.04/6.97 | 0.650/2.05/6.95 |
| Formula 5 | 0.643/2.00/7.12 | 0.654/2.05/7.04 | 0.652/2.06/7.03 |
| Comparison example 1 | aggregate | aggregate | aggregate |
| Comparison example 2 | aggregate | aggregate | aggregate |

TABLE 3

Aripiprazole particle size in suspensions under 40° C. measured 0, 1, 2, 3 months

|  | 40° C., 0 h | 40° C., 1 month | 40° C., 2 months | 40° C., 3 months |
| --- | --- | --- | --- | --- |
| Formula 1 | 0.606/1.93/7.16 | 0.712/2.17/7.39 | 0.743/2.23/8.27 | 0.770/2.35/9.20 |
| Formula 2 | 0.624/1.84/5.00 | 0.702/1.96/5.53 | 0.750/2.10/5.98 | 0.751/2.03/5.96 |
| Formula 3 | 0.461/1.27/4.11 | 0.472/1.27/4.41 | 0.482/1.27/4.27 | 0.479/1.28/4.22 |
| Formula 4 | 0.604/1.92/6.99 | 0.691/2.11/7.51 | 0.707/2.14/7.60 | 0.713/2.13/7.66 |
| Formula 5 | 0.603/1.90/6.85 | 0.682/2.10/7.38 | 0.705/2.27/11.1 | 0.703/2.17/8.73 |
| Comparison example 1 | 0.527/1.43/4.04 | aggregate | aggregate | aggregate |
| Comparison example 2 | 0.588/1.77/5.98 | 0.731/2.10/7.24 | aggregate | aggregate |

TABLE 4

Aripiprazole particle size in suspensions under 60° C. measured 10, 20, 30 days

| | 60° C., 0 h | 60° C., 10 days | 60° C., 20 days | 60° C., 30 days |
|---|---|---|---|---|
| Formula 1 | 0.606/1.93/7.16 | 0.762/2.39/10.8 | 0.796/2.41/8.47 | 0.791/2.40/8.21 |
| Formula 2 | 0.624/1.84/5.00 | 0.768/2.11/5.95 | 0.798/2.18/6.22 | 0.797/2.22/6.22 |
| Formula 3 | 0.461/1.27/4.11 | 0.495/1.31/4.26 | 0.503/1.32/4.37 | 0.505/1.31/4.40 |
| Formula 4 | 0.604/1.92/6.99 | 0.760/2.33/8.10 | 0.781/2.35/8.36 | 0.768/2.36/8.48 |
| Formula 5 | 0.603/1.90/6.85 | 0.760/2.35/8.80 | 0.764/2.40/9.63 | 0.755/2.36/8.41 |
| Comparison example 1 | 0.527/1.43/4.04 | 0.707/1.92/6.34 | aggregate | aggregate |
| Comparison example 2 | 0.588/1.77/5.98 | 0.713/2.14/9.17 | 0.716/2.35/8.31 | aggregate |

Conclusion: The results in tables 2 to 4 show that the particles do not easily aggregate and settle from the aripiprazole suspension of the present invention after storage for a long time, and can be redispersed, overcoming the problems in the prior art.

Example 3: Pharmacokinetics in SD Rats

The aripiprazole suspension of the present invention was injected into the thigh muscle of SD rats to examine the pharmacokinetics of the drug in SD rats and compared with commercially available Abilify Maintena, so as to evaluate the slow release effects of the aripiprazole suspension of the present invention.

In this example, male SD rats (SPF grade) weighing 230-250 g purchased from Shanghai Slack Laboratory Animal Co., Ltd were used. Throughout the experiment, rats have free access to water.

The testing SD rats were randomly divided into experimental group and control group (i.e., Abilify Maintena group). Each group was administered intramuscularly (i.m.) with drug at a dose of 25 mg/kg. The formula and preparation of drug for the experimental group were the same as described in Example 1 (D90 of aripiprazole does not exceeds 30 μm).

SD rats were fasted 12 hours (h) before administration of drug, and fed 4 h after administration of drug. After administration of drug, 0.5 ml of venous blood was collected from plexus basal veins at 6, 24, 72, 144, 216, 336, 504, 672, 840, and 1008 hours, and placed in a pre-labeled EDTA (4 mM) anticoagulant EP tube, and then placed on ice. The plasma was collected by centrifugation under 4° C., 8000 rpm and 5 min, and transferred to a 96-well plate and stored at −20° C. until LC-MS/MS analysis. The concentration of drug in EDTA (4 mM) anticoagulated SD rats plasma was determined using LC/MS/MS (Agilent 6460) method. The concentration-time curves of the experimental and control groups are shown in FIG. 1.

Conclusion: The rats were monitored for up to 1008 h after a single administration, and the suspensions of the present invention had similar sustained release effects to the commercial product (Abilify Maintena).

The foregoing are only preferred embodiments of the present invention. It is to be noted that several improvements and modifications may be made by persons having ordinary skill in the art without departing from the principles of the present invention. These improvements and modifications should be deemed as the scope of protection of the present invention.

What is claimed is:

1. An aripiprazole injectable suspension formulation having prolonged shelf life, comprising aripiprazole in an amount of 200 mg/mL;
   sodium carboxymethyl cellulose in an amount selected from 4 mg/mL or 8 mg/mL;
   mannitol in an amount of 40 mg/mL;
   polyoxyethylene (20) sorbitan monooleate in an amount selected from 4 mg/mL, 8 mg/mL or 24 mg/mL; and
   sodium dihydrogen phosphate in an amount of 0.6 mg/mL.

2. A method for treating schizophrenia, comprising:
   administering the aripiprazole injectable suspension formulation according to claim 1 to a subject in need thereof.

3. The method of claim 2, wherein the aripiprazole injectable suspension formulation is administered intramuscularly or subcutaneously.

4. A method of prolonging shelf life of an aripiprazole injectable suspension formulation, comprising
   dispersing aripiprazole in a vehicle for injection,
   wherein the aripiprazole is in an amount of 200 mg/mL, and the vehicle contains sodium carboxymethyl cellulose in an amount selected from 4 mg/mL or 8 mg/mL, mannitol in an amount of 40 mg/mL, polyoxyethylene (20) sorbitan monooleate in an amount selected from 4 mg/mL, 8 mg/mL or 24 mg/mL, and sodium dihydrogen phosphate in an amount of 0.6 mg/mL.

* * * * *